United States Patent [19]

Mormann et al.

[11] Patent Number: 4,886,902

[45] Date of Patent: Dec. 12, 1989

[54] PROCESS FOR THE PREPARATION OF ISOCYANATES AND THEIR USE FOR THE PREPARATION OF POLYISOCYANATES CONTAINING ESTER GROUPS

[75] Inventors: Werner Mormann, Kreustal; Gabriele Leukel, Norken, both of Fed. Rep. of Germany

[73] Assignee: Bayer Aktiengesellschaft, Leverkusen, Fed. Rep. of Germany

[21] Appl. No.: 368,750

[22] Filed: Jun. 20, 1989

Related U.S. Application Data

[62] Division of Ser. No. 241,438, Sep. 7, 1988.

[30] Foreign Application Priority Data

Sep. 16, 1987 [DE] Fed. Rep. of Germany ....... 3730986

[51] Int. Cl.$^4$ ............................................. C07C 69/76
[52] U.S. Cl. ..................................... 560/106; 560/109
[58] Field of Search ................................ 560/106, 109

[56] References Cited

U.S. PATENT DOCUMENTS

| | | | |
|---|---|---|---|
| 2,611,782 | 9/1952 | Bortnick | 560/334 |
| 4,292,255 | 9/1981 | Hennig et al. | 560/336 |
| 4,654,428 | 3/1987 | Kurashima | 556/414 |

OTHER PUBLICATIONS

Noll, Chem. and Tech. of Silicones, (1968), p. 86.

*Primary Examiner*—Alan Siegel
*Attorney, Agent, or Firm*—Joseph C. Gil; Richard E. L. Henderson

[57] ABSTRACT

This invention relates to a novel process for the preparation of isocyanates containing silylated alcoholic or phenolic hydroxyl groups as substituents and to the use of the compounds obtained by this process as reactants for isocyanatocarboxylic acid halides in the preparation of polyisocyanates containing ester groups.

1 Claim, No Drawings

PROCESS FOR THE PREPARATION OF ISOCYANATES AND THEIR USE FOR THE PREPARATION OF POLYISOCYANATES CONTAINING ESTER GROUPS

This application is a division of application Ser. No. 07/241,438 filed Sept. 7, 1988

BACKGROUND OF THE INVENTION

This invention relates to a novel process for the preparation of isocyanates containing silylated hydroxyl groups or silylated carboxyl groups as substituents and to the use of the compounds obtained by this process as reactants for isocyanatocarboxylic acid halides in the preparation of polyisocyanates containing ester groups.

The preparation of organic isocyanates containing silylated alcoholic hydroxyl groups as substituents is known. Silyloxyalkyl isocyanates, for example, are obtained by reaction of the amino alcohols corresponding to the isocyanates with bis(3-chlorophenyl) carbonate to produce N-(2-hydroxyalkyl)carbamic acid 4-chlorophenyl ester; silylation of the reaction product with trimethylchlorosilane in the presence of an equimolar quantity of triethylamine; and decomposition of the resulting carbamic acid ester. H. R. Kricheldorf, *Liebigs Annalen der Chemie* (1973), 772.

The preparation of aromatic isocyanates containing silylated phenolic hydroxyl groups as substituents by thermal decomposition of the corresponding O-phenylurethanes has also been described by H. R. Kricheldorf, see above reference. The ester used for this purpose must be prepared from N,O-bis-silylated aminophenols and chloroformic acid phenyl ester in the presence of triethylamine.

Another process for the preparation of isocyanates containing silylated hydroxyl groups is based on the rection of trimethylsilyloxybenzoyl chloride with trimethylsilyl azide, the isocyanates being formed by Curtius degradation of the acid azides. The process is limited to trimethylsilyloxyaryl isocyanates because trimethylsilyoxyalkanoyl chlorides cannot be prepared. G. Schwarz, H. Alberts, H. R. Kricheldorf, *Liebigs Annalen der Chemie* (1981), 1257.

All of these processes known in the art are cumbersome multistage processes that are not generally applicable and that have hitherto been described only in the scientific literature, without significant practical technology having been demonstrated.

It has now surprisingly been found that organic isocyanates containing silylated hydroxyl groups or silylated carboxyl groups, preferably alcoholic or phenolic hydroxyl groups as substituents may easily be obtained by reaction at elevated temperatures of the corresponding O-silylated amino phenols, amino alcohols or aminocarboxylic acids with at least equivalent quantities of non-volatile organic polyisocyantes. The O-silylated starting materials used for this reaction may in turn be obtained by a simple reaction of the corresponding amino phenols, amino alcohols or aminocarboxylic acids with hexamethyldisilazane (HMDS),

SUMMARY OF THE INVENTION

The present invention relates to a process for the preparation of isocyanate compounds substituted with one or more silylated hydroxyl groups or silylated carboxyl groups, preferably silylated alcoholic or phenolic hydroxyl groups comprising heating in a temperature range of from about 20° C. to about 300° C., optionally at reduced pressure, a mixture of (i) amine precursors corresponding to said isocyanate compounds substituted with one or more silylated hydroxyl groups or silylated carboxyl groups, and (ii) at least about one to about 20 molar quantities of organic polyisocyanates that are essentially nonvolatile under the conditions of the process.

The products of the process are recovered in the form of the distillate obtained during the course of the reaction.

The amine precursors used as component (i) in the process according to the invention may be hydroxyl amine or any primary amines that are substituted with at least one silylated alcoholic or phenolic hydroxyl group or at least one silylated carboxylic group and which are suitable for conversion to corresponding isocyanates. Particularly suitable starting materials are compounds corresponding to the following formulas:

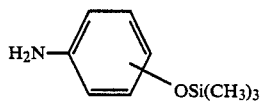

or

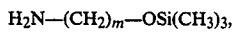

wherein m is zero or an integer of from 2 to 4.

Suitable O-silylated amino phenols are also those which carry inert substituents in the 2-position to the amino group. Possible inert substituents are chlorine, bromine, nitro, alkyl groups with 1–20, preferably 1–4 carbon atoms, alkoxy groups with 1–20, preferably 1–4 carbon atoms and alkoxy carbonyl groups with 1–20, preferably 1–4 carbon atoms in the alkoxy moiety.

The following, for example, are suitable amine precursors: 2-, 3- and 4-(trimethylsilyloxy)aniline, 2-(trimethylsilyloxy)ethylamine, 3-(trimethylsilyloxy)propylamine and 4-(trimethylsilyloxy)butylamine. Also suitable are, for example, 1-(2-aminoethoxy)-2-trimethylsilyloxyethane, 1,1-dimethyl-2-trimethylsilyloxyethylamine, trimethyl siloxy amine, 4-(trimethylsiloxy)-cyclohexyl amine, 4-aminobenzoic acid trimethylsilylester or 2-methyl-4-trimethylsiloxyphenylamine. The corresponding compounds in which some or all of the substituents on the silicon atom are higher alkyl groups, such as ethyl, propyl or butyl groups instead of the methyl group, are also suitable but less preferred.

O-Silylated aminophenols and amino alcohols of this type may be prepared, for example, by a method analogous to that described by E. Lukevits et al in *Zh. Obshch. Khim*, 39, 806 (1969) by monosilylation of the amino phenols or amino alcohols using hexaalkyldisilazane, preferably hexamethyldisilazane (HMDS). The reaction may be carried out, for example, by heating the amino phenols or amino alcohols with HMDS in proportions corresponding to a molar ratio of hydroxyl groups to HMDS of from 1:0.5 to 1:0.6 at temperatures of up to 170° C. (preferably 50° to 170° C.) in the presence of a catalytic quantity of trimethylchlorosilane. Selective silylation of the hydroxyl groups, with concomitant elimination of ammonia, occurs.

The essentially non-volatile polyisocyanates used as component (ii) in the process according to the invention are high boiling polyisocyanates. As used herein the term "high boiling polyisocyanates" includes organic polyisocyanates that do not boil under the conditions employed for the process according to the invention. That is, they are either non-distillable polyisocyanates or high boiling polyisocyanates having a boiling point preferably at least 20° C. above the boiling point of the product of the process. Any organic polyisocyanates which satisfy these conditions are suitable in principle but appropriate aromatic polyisocyanates are preferred. Particularly suitable polyisocyanates are, for example, the polyisocyanates or polyisocyanate mixtures of the diphenylmethane series, such as 4,4'-diisocyanatodiphenylmethane; mixtures thereof with 2,4'- and, optionally, 2,2'-diisocyanatodiphenylmethane; or polyisocyanate mixtures which contain higher nuclear polyisocyanates in addition to the above isomers, such as the mixtures obtained from the phosgenation of aniline-formaldehyde condensates. Aliphatic polyisocyanates, such as hexamethylene diisocyanate or isophorone diisocyanate, are also suitable in principle.

The polyisocyanates (ii) are used in at least equivalent quantities in the process according to the invention. This means that at least about 1, preferably at least 1.1, and more preferably up to 20, isocyanate groups of component (ii) are available for each amino group of component (i). Although an even greater excess of component (ii) could in principle be used, the yield would not increase.

DETAILED DESCRIPTION OF THE INVENTION

The process according to the invention may be carried out, for example, by introducing polyisocyanate component (ii) into a suitable reaction vessel equipped with stirrer and distillation bridge and adding component (i) portion-wise with stirring within the temperature range of from 20° to 300° C., preferably from 20° to 200° C., and more preferably starting at about 100° to 140° C. and then heating to 200° C. after all of component (ii) has been added. The product of the process, which forms spontaneously, is then recovered as distillate, optionally under vacuum. Alternatively, components (i) and (ii) may be mixed together at a lower temperature, followed by heating to 200° C., optionally at pressures below atmospheric pressure. The resulting product of the process may at the same time be recovered as distillate.

The preferred products of the process according to the invention corrrespond to the following formulas:

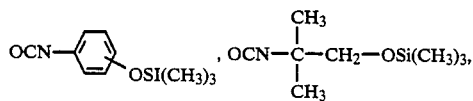

or

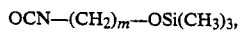

wherein m is zero or an integer of from 2 to 4.

The products of the process according to the invention which carry silylated alcoholic or phenolic hydroxy groups are valuable intermediate products for the preparation of polyisocyanates containing ester groups. These may in turn be used as polyisocyanate components for the production of polyurethanes.

For this use according to the invention, said products according to the invention are reacted with isocyanatocarboxylic acid halides, preferably isocyantocarboxylic acid chlorides. Suitable isocyanatocarboxylic acid chlorides include compounds corresponding to the following general formula

wherein

R is an aliphatic hydrocarbon group with 1 to 5 carbon atoms or an aromatic hydrocarbon group with 6 to 10 carbon atoms, wherein at least 2 carbon atoms are arranged between the isocyanate groups and the chlorocarbonyl group.

Examples of such particularly preferred isocyanatocarboxylic acid chlorides include 3-isocyanatopropionic acid chloride, 4-isocyanatobutyric acid chloride, 3-isocyanatobenzoic acid chloride, and 4-isocyanatobenzoic acid chloride.

In addition to these particularly preferred isocyanatocarboxylic acid chlorides, those corresponding to the general formula OCN—R—COCl in which R stands for an aliphatic hydrocarbon group containing more than 6 carbon atoms or a cyloaliphatic hydrocarbon group may also be used. Examples of such isocyanatocarboxylic acid chlorides include 12-isocyanatododecanoic acid chloride and 4-isocyanatocyclohexanecarboxylic acid chloride.

It is also possible to use isocyanatobenzoic acid chlorides which carry inert substituents in the 2-position relative to the isocyanate group. Possible inert substituents are those already mentioned hereinbefore in connection with the amino phenols.

Isocyanatocarboxylic acid chlorides which contain more than one isocyanate group or more than one carboxylic acid chloride group are also suitable. These include, for example, 2,4-diisocyanatobenzoic acid chloride, and 2,6-diisocyanatocaproic acid chloride, and 2-isocyanatoglutaric acid dichloride. Such compounds containing more than one isocyanate or chlorocarbonyl group are, however, less preferred.

The products of the process according to the invention which carry silylated carboxylic groups can easily be converted into the corresponding isocyanato carboxylic acid chlorides by reacting them with chlorination agents such as POCl$_3$ or SOCl$_2$.

When the products of the process according to the invention carrying silylated alcoholic or phenolic hydroxyl groups are used as reactants with the isocyanatocarboxylic acid chlorides exemplified above (i.e., in the process for the preparation of polyisocyanates containing ester groups using the above-mentioned products of this process as starting materials), the quantity of reactants is generally chosen to provide at least 0.8 mole of silylated hydroxyl groups for each mole of chlorocarbonyl groups. The quantities of reactants are preferably chosen to provide from 0.8 to 1.2 mole of silylated hydroxyl groups for each mole of chlorocarbonyl groups. It is particularly preferred to use equimolar quantities (i.e., wherein the molar ratio of the above mentioned reactive groups is 1:1). Although one of the two components could be used in an excess outside the range of 0.8 to 1.2 mole, doing so would merely reduce the yield.

The ester-forming reaction is generally carried out within the temperature range of from 50° to 170° C. The end of the reaction can easily be detected (if no excess of acid chloride has been used) by the disappearance of the acid chloride carbonyl band at 1800 cm$^{-1}$ in the infrared spectrum.

The ester-forming reaction may be carried out with the aid of suitable catalysts. Such catalysts are added in quantities of from 0.1 to 10% by weight, preferably from 0.1 to 2% by weight, based on the weight of the reactants. Suitable catalysts include Lewis acids, such as titanium trichloride, tin dichloride, and zinc chloride; acids such as sulfuric acid; or bases such as 4-dimethylaminopyridine.

The ester-forming reaction may be carried out with or without a suitable solvent. Suitable solvents are, for example, diethyl ether, toluene, xylene, chlorobenzene, o-dichlorobenzene, trichloroethylene, ethyl acetate, butyl acetate, and any mixtures of such solvents.

The polyisocyanates containing ester groups thereby obtained from the products of the process according to the invention are valuable starting materials for the preparation of polyurethane plastics. The corresponding compounds containing aliphatically or cycloaliphatically bound isocyanate groups are eminently suitable for the production of one-component or two-component polyurethane lacquers. The functionality of the polyisocyanates which contain ester groups may be adapted to the intended use not only by choosing suitable starting materials used for their preparation but also by using mixtures of different starting materials.

Ester diisocyanates based on aromatic isocyanatocarboxylic acid chlorides and silylated isocyanatophenols occasionally also have interesting liquid crystalline properties.

The following examples further illustrate details for the process of this invention. The invention, which is set forth in the foregoing disclosure, is not to be construed or limited either in spirit or in scope by these examples. Those skilled in the art will readily understand that known variations of the conditions of the following reparative procedures can be used in the process of this invention. All temperatures are degrees Celsium unless otherwise noted. All percentages are percentages by weight.

DESCRIPTION OF THE PREFERRED EMBODIMENTS

Example 1

Preparation of O-silylated starting materials

The amino compound containing hydroxyl or carboxyl groups (1mole) is introduced into a 500-ml three-necked flask with magnetic stirring bar, internal thermometer, dropping funnel, and reflux condenser, as well as with bubble counter, drying tube, and gas discharge tube, Hexamethyldisilazane (0.55 mole) is rapidly added dropwise. After the addition of three drops of trimethylchlorosilane as catalyst, the liquid mixture, which is in some cases heterogeneous, is slowly heated. Evolution of ammonia becomes noticeable at 50° to 55° C. and becomes very vigorous at 85° to 95° C. for amino alcohols and at 130° C. for amino phenols. The temperature is raised to 140° to 170° C., where it is maintained until gas evolution ceases (3 to 7 hours). The homogeneous liquid is then purified by rectifying using a mirrored vigreux column.

The method is illustrated by following compounds:

Example 1.1

4-trimethylsilyloxyphenylamine

Yield: 88.6%
bp: 114°–116° C. (20 mbar)
$n_D^{20}$: 1.5189

Example 1.2

3-trimethylsilyloxyphenylamine

Yield: 81%
bp: 115°–116° C. (20 mbar)

Example 1.3

4-trimethylsilyloxybutylamine

Yield: 83%
bp: 63°–64° C. (20 mbar)
IR spectrum: 3380 and 3300 cm$^{-1}$ (NH stretching vibration), 1600 cm$^{-1}$ (NH bending vibration)
Elemental analysis (%): Calculated: C, 51.44; H, 11.6; N, 6.0. Found: C, 51.40; H, 11.1; N, 5.8.

Example 1.4

3-trimethylsilyloxypropylamine

Yield: 75%
bp: 134°–135° C. (495 mbar)
$n_D^{20}$: 1.4195
IR spectrum: 3390 and 3340 cm$^{-1}$ (NH stretching vibration), 1600 cm$^{-1}$ (NH bending vibration)
$^1$H NMR spectrum: 3.45 (t, 2H); 2.55 (t, 2H); 1.45 (m, 2H); 0.85 (s, 2H) ppm

Example 1.5

2-trimethylsilyloxyethylamine

Yield: 83%
bp: 38°–39° C. (20 mbar)
$n_D^{20}$: 1.4131
IR spectrum: 3380 and 3300 cm$^{-2}$ (NH stretching vibration), 1590 cm$^{-2}$ (NH bending vibration)

Example 1.6

2-trimethylsilyloxy-2-methylpropylamine

Yield: 85%
bp: 38°–38.5° C. (20 mbar)
$n_D^{20}$: 1.4089
IR spectrum: 3380 and 3280 cm$^{-1}$ (NH stretching vibration), 1590 cm$^{-1}$ (NH bending vibration)

Example 1.7 trans-4-trimethylsiloxy-cyclohexylamine

Yield: 88%
bp: 81°–83° C. (20 mbar)
$n_D^{20}$: 1.4511
IR spectrum: 3365 and 3280 cm$^{-1}$

Example 1.8 trimethylsiloxyamine

Yield: 51%
bp: 99°–100° C.
$n_D^{20}$: 1.4010
IR spectrum: 3370 and 3280 cm$^{-1}$

Example 1.9

4-aminobenzoic acid trimethylsilylester Yield: 91%
bp: 110° C. (0.015 mbar)

mp: 62° C.
IR spectrum: 3370 and 1730 cm$^{-1}$

Example 1.10

2-methyl-4-trimethylsiloxyphenylamine

Yield: 94%
bp: 121° C. (20 mbar)
IR spectrum: 3460, 3370 and 3280 cm$^{-1}$

Example 2

Process according to the invention (general method of preparation)

4,4-Diisocyanatodiphenylmethane (500 g, 2 mole) is weighed into a 500-ml glass flask equipped with magnetic stirring bar, internal thermometer, dropping funnel and distillation bridge, with a 100 ml nitrogen flask as receiver. After the diisocyanate compound is melted under argon, trimethylsilyloxyaryl(alkyl)amine (0.4 mole) is slowly introduced dropwise at 110° to 120° C., accompanied by formation of white mists. When all of the amine has been added, the apparatus is carefully evacuated while being further heated to 200° C. The colorless liquid which distills over is then fractionated. The method is illustrated by the following compounds:

Example 2.1

4-trimethylsilyloxyphenylisocyanate

Yield: 95%
bp: 52°-53° C. (0.24 mbar)
$n_D^{20}$: 1.5032
IR spectrum: 2280 cm$^{-1}$ (N=C=O)
$^1$H NMR spectrum: 6.92 (m, 4H); 0.31 (s, 9H) ppm
Elemental analysis (%): Calculated: C, 58.0; H, 6.3; N, 6.8. Found: C, 58.4; H, 6.2; N, 7.2.

Example 2.2

3-trimethylsilyloxyphenylisocyanate

Yield: 79%
bp: 109° C. (20 mbar)
$n_D^{20}$: 1.5025
IR spectrum: 2280 cm$^{-1}$ (N=C=O)
$^1$H NMR spectrum: 6.93 (m, 4H); 0.34 (s, 9H) ppm
Elemental analysis (%): Calculated: C, 58.0; H, 6.3; N, 6.8. Found: C, 57.9; H, 6.4; N, 6.7.

Example 2.3

4-trimethylsilyloxybutylisocyanate

Yield: 70%
bp: 75°-76° C. (20 mbar)
$n_D^{20}$: 1.4250
IR spectrum: 2270 cm$^{-1}$ (N=C=O)
$^1$H NMR spectrum: 3.58 (t, 2H); 3.27 (t, 2H); 1.58 (m, 4H); 0,05 (s, 9H) ppm.
Elemental analysis (%): Calculated: C, 51.3; H, 911; N, 7.5. Found: C, 50.4; H, 9.0; N, 7.4.

Example 2.4

3-trimethylsilyloxypropylisocyanate

Yield: 94%
bp: 68.5°-69° C. (20 mbar)
$n_D^{20}$: 1.4200
IR spectrum: 2280 cm$^{-1}$ (N=C=O)
$^1$H NMR spectrum: 3.65 (t, 2H); 3.39 (t, 2H); 1.78 (m, 2H); 0,09 (s, 9H) ppm.
Elemental analysis (%): Calculated: C, 48.5; H, 8.7; N, 8.1. Found: C, 48.9; H, 9.7; N, 8.2.

Example 2.5

2-trimethylsilyloxyethylisocyanate

Yield: 84%
bp: 45° C. (20 mbar)
$n_D^{20}$: 1.4140
IR spectrum: 2280 and 2240 cm$^{-1}$ (N=C=O)
$^1$NMR spectrum: 3.68 (t, 2H); 3.30 (t, 2H); 0.17 (s, 9H) ppm
Elemental analysis (%): Calculated: C, 45.2; H, 8.2; N, 8.8. Found: C, 44.7; H, 7.6; N, 8.8.

Example 2.6

2-trimethylsilyloxy-2-methylpropylisocyanate

Yield: 96%
bp:
57° C.
$n_D^{20}$: 1.4011
IR spectrum: 2260 cm$^{-1}$ (N=C=O)
$^1$NMR spectrum: 3.40 (s, 2H); 1.22 (s, 6H); 0.12 (s, 2H) ppm
Elemental analysis (%): Calculated: C, 51.3; H, 9.2; N, 7.5. Found: C, 51.9; H, 9.3; N, 7.6.

Example 2.7 trans-4-trimethylsilyloxycyclohexylisocyanate

Yield: 93%
bp: 96°-98° C. (20 mbar)
$n_D^{20}$: 1.4492
IR spectrum: 2275 cm$^{-1}$ Elemental Analysis (%)

Calculated: C, 65,3; H, 9,00; N, 6,57. Found: C, 55,9; H, 9,05; N, 6,5.

Example 2.8 trimethylsiloxyisocyanate

Yield: 67%
bp: 105° C.
$n_D^{20}$: 1.3618
IR spectrum: 2280 cm$^{-1}$

Example 2.9

4-isocyanatobenzoic acid trimethylsilylester

Yield: 88%
bp: 85° C. (0.03 mbar)
mp: 48° C.
IR spectrum: 2280 and 1730 cm$^{-1}$

Example 2.10

2-methyl-4-trimethylsiloxyphenylisocyanate

Yield: 90%
bp: 67°-68° C. (0.06 mbar)
$n_D^{20}$: 1.5056
IR spectrum: 2280 cm$^{-1}$

Example 3

Use according to the invention (general method)

Trimethylsilyloxyphenyl-, trimethylsilyloxyethyl- or trimethylsilyloxybutylisocyanate (4 mole) is introduced into a 25-ml round bottomed flask equipped with magnetic stirring bar, microdistillation bridge, drying tube and receiver. An equivalent molar quantity of 6-isocyanatohexanoic acid chloride or 3-isocyanatopropanoic acid chloride is added by a pipette. The reaction mixture is heated to 130° C. and kept at this temperature with stirring until the reaction is completed (about 24 hours). The liquid is purified in a bulb-tube distillation apparatus.

Example 3.1

Use according to the invention as reactant for 6-isocyanatocaproic acid chloride The method is illustrated by the following compounds:

Example 3.1.1

6-isocyanatocaproic acid 4-isocyanatophenyl ester

Yield: 72%
bp: 160°–180° C. (0.37 mbar)
$n_D^{20}$: 1.5235
IR spectrum: 2280 cm$^{-1}$ (N=C=O), 1755 cm$^{-1}$ (COO)
$^1$H NMR spectrum: 7.02 (s, 4H); 3.30 (t, 2H); 2.55 (t, 2H); 1.56 (m, 2H) ppm
Elemental analysis (%): Calculated: C, 61.3; H, 5.1; N, 10.2. Found: C, 61.1; H, 5.1; N, 10.6.

Example 3.1.2

6-isocyanatocaproic acid 3-isocyanatophenyl ester

Yield: 75%
bp: 170° C. (0.05 mbar)
$n_D^{20}$: 1.5240
IR spectrum: 2280 cm$^{-1}$ (N=C=O), 1755 cm$^{-1}$ (COO)
$^1$H NMR spectrum: 7.03 (m, 4H); 3.24 (t, 2H); 2.42 (t, 2H); 1.59 (m, 6H) ppm
Elemental analysis (%): Calculated: C, 61.3; H, 5.1; N, 10.2. Found: C, 61.4; H, 5.2; N, 10.3.

Example 3.1.3

6-isocyanatocaproic acid 4-isocyanatobutyl ester

Yield: 85%
bp: 165°–170° C. (0.07 mbar)
$n_D^{20}$: 1.4620
IR spectrum: 2280 cm$^{-1}$ (N=C=O), 1735 cm$^{-1}$ (COO).
$^1$H NMR spectrum: 4.09 (t, 2H); 3.34 (t, 4H); 2.32 (t, 2H); 1.63 (m, 10H) ppm.
Elemental analysis (%): Calculated: C, 56.7; H, 7.1; N, 11.0. Found: C, 56.8; H, 7.0; N, 11.3.

Example 3.1.4

6-isocyanatocaproic acid 2-isocyanatoethyl ester

Yield: 31%
bp: 150°–160° C. (0.1 mbar)
IR spectrum: 2280 cm$^{-1}$ (COO)
$^1$H NMR spectrum: 4.19 (t, 2H); 3.50 (t, 2H); 3.30 (t, 2H); 2.38 (t, 2H); 1.57 (m, 6H) ppm

Example 3.2

Use according to the invention as reactant for 3-isocyanatopropionic acid chloride The method is illustrated by the following compounds:

Example 3.2.1

3-isocyanatopropionic acid 4-isocyanatophenyl ester

Yield: 70%
bp: 160° C. (0.04 mbar)
$n_D^{20}$: 1.5377
IR spectrum: 2270 cm$^{-1}$ (N=C=O), 1750 cm$^{-1}$ (CO)
$^1$H NMR spectrum: 7.50 (s, 4H); 3.63 (t, 2H); 2.79 (t, 2H) ppm
Elemental analysis (%): Calculated: C, 56.4; H, 4.2; N, 12.0. Found: C, 56.9; H, 3.7; N, 12.1.

Example 3.2.2

3-isocyanatopropionic acid 3-isocyanatophenyl ester

Yield: 72%
bp: 150°–190° C. (0.03 mbar)
mp: 45°–46° C.
IR spectrum: 2285 cm$^{-1}$ (N=C=O), 1760 cm$^{-1}$ (COO)
$^1$NMR spectrum: 7.32 (m, 2H); 6.97 (m, 2H); 3.73 (t, 2H); 2.86 (t, 2H) ppm
Elemental analysis (%): Calculated: C, 56.4; H, 3.4; N, 12.0. Found: C, 56.7; H, 3.8; N, 11.8.

Example 3.2.3

3-isocyanatopropionic acid 4-isocyanatobutyl ester

Yield: 60%
bp: 150°–170° C. (0.05 mbar)
$n_D^{20}$: 1.4598
IR spectrum: 2280 cm$^{-1}$ (N=C=O), 1735 cm$^{-1}$ (COO).
$^1$H NMR spectrum: 4.18 (5, 2H); 3.46 (m, 4H); 2.60 (t, 2H); 1.71 (t, 4H) ppm
Elemental analysis (%): Calculated: C, 50.9; H, 5.7; N, 13.2. Found: C, 50.8; H, 6.0; N, 13.4.

Example 3.3

Use according to the invention as reactant for 4-isocyanatobenzoyl chloride and 3-isocyanatobenzoyl chloride The general method of Example 3 is modified in that 10 ml of o-dichlorobenzene is used as solvent and the reaction mixture is heated at 165° C. to the end of the reaction in the presence of 0.1% catalyst. After the solvent has been drawn off, the products are purified by distillation in a bulb-tube distillation apparatus. The method is illustrated by the compounds in the following table.

| No. | Diisocyanate | Catalyst | Heating temperature for bulb-tube distillation °C. | Yield (%) | Melting point (°C.) | IR-bands[2] (cm$^{-1}$) | Elemental analysis (%) Calculated | Found |
|---|---|---|---|---|---|---|---|---|
| 3.3.1 | OCN—⟨C$_6$H$_4$⟩—C(=O)—O—⟨C$_6$H$_4$⟩—NCO | TiCl$_3$ | 180–200 | 68 | K 117.5 n 150 i | 2320, 1740 | C: 64.3 H: 2.9 N: 10.0 | 64.4 2.9 10.0 |

-continued

| No. | Diisocyanate | Catalyst | Heating temperature for bulb-tube distillation °C. | Yield (%) | Melting point (°C.) | IR-bands[2] (cm$^{-1}$) | Elemental analysis (%) Calculated | Found |
|---|---|---|---|---|---|---|---|---|
| 3.3.2 | OCN—⌬—C(O)—O—⌬—NCO | TiCl$_3$ | 180 | 90 | K 91.8 i | 2300, 1745 | C: 64.3 H: 2.9 N: 10.0 | 64.5 2.9 10.0 |
| 3.3.3 | OCN—⌬—C(O)—O—⌬—NCO | ZnCl$_2$ | 190 | 30 | K 106 i | 2310, 1740 | C: 64.3 H: 2.9 N: 10.0 | 64.4 2.9 10.0 |
| 3.3.4 | OCN—⌬—C(O)—O—⌬—NCO | TiCl$_3$ TiCl$_4$ H$_2$SO$_4$ ZnCl$_2$ DMAP[1] | 150–160 | 86 75 80 36 50 | K 69 i | 2280, 1745 | C: 64.3 H: 2.9 N: 10.0 | 64.4 3.0 10.1 |

[1] 4-dimethylamino-pyridine
[2] K = crystalline, n = nematic, i = isotropic

Example 4
Use according to the invention

Following the general method of Example 3 the diisocyanates 4.1 through 4.3 as set forth in the following table are made.

boxylic acid halide with an isocyanate compound substituted with one or more silylated alcoholic or phenolic hydroxyl groups prepared by heating, in a temperature range of from about 20° C. to about 300° C., a mixture of (i) an amine precursor corresponding to said isocya-

| No. | Diisocyanate | cat. | heating temperature for bulb distillation (°C.) | Yield (%) | Melting point (°C.) | IR-bands in cm$^{-1}$ | Elemental analysis Calculated | found |
|---|---|---|---|---|---|---|---|---|
| 4.1 | OCN—⌬(CH$_3$)—C(O)—O—⌬—NCO | H$_2$SO$_4$ | 180 | 95 | K 81 a[1] 73 i | 2300, 1740 | C: 65.31 H: 3.43 N: 9.52 | 65.5 3.6 9.6 |
| 4.2 | OCN—⌬—C(O)—O—⌬(CH$_3$)—NCO | H$_2$SO$_4$ | 180 | 92 | K 71.5 a 66 i | 2280, 1725 | C: 65.31 H: 3.43 N: 9.52 | 65.7 3.5 9.7 |
| 4.3 | OCN—⌬—C(O)—O—⌬—NCO | TiCl$_4$ | 160 | 20 | K 66 a 14 i | 2280, 1710 | C: 63.99 H: 5.37 N: 9.32 | 63.7 5.6 9.4 |

[1] a = anisotropic

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a polyisocyanate containing ester groups comprising reacting an isocyanate-carnate compound substituted with silylated hydroxyl groups, and (ii) at least one to about 20 molar quantities of an organic polyisocyanate that is essentially non-volatile under the conditions used in preparing said isocyanate compound substituted with silylated hydroxyl groups.

* * * * *